(12) United States Patent
Riebel et al.

(10) Patent No.: US 11,758,925 B2
(45) Date of Patent: Sep. 19, 2023

(54) CONTINUOUS PRODUCTION OF AN ADSORPTION PRODUCT OF A NITROOXY-FUNCTIONAL ORGANIC COMPOUND

(71) Applicant: DSM IP ASSETS B.V., Te Heerlen (NL)

(72) Inventors: Peter Riebel, Kaiseraugst (CH); Kai Urban, Kaiseraugst (CH)

(73) Assignee: DSM IP ASSETS B.V., Te Heerlen (NL)

( * ) Notice: Subject to any disclaimer, the term of this patent is extended or adjusted under 35 U.S.C. 154(b) by 33 days.

(21) Appl. No.: 17/257,763

(22) PCT Filed: Jul. 12, 2019

(86) PCT No.: PCT/EP2019/068855
§ 371 (c)(1),
(2) Date: Jan. 4, 2021

(87) PCT Pub. No.: WO2020/011992
PCT Pub. Date: Jan. 16, 2020

(65) Prior Publication Data
US 2021/0120844 A1    Apr. 29, 2021

(30) Foreign Application Priority Data

Jul. 12, 2018   (EP) .................................... 18183246

(51) Int. Cl.
*A23K 20/105* (2016.01)
*A23K 20/28* (2016.01)
(Continued)

(52) U.S. Cl.
CPC ............ *A23K 20/105* (2016.05); *A23K 20/28* (2016.05); *A23K 50/10* (2016.05); *C07C 203/04* (2013.01)

(58) Field of Classification Search
CPC ...... A23K 20/105; A23K 20/28; A23K 50/10; C07C 203/04
See application file for complete search history.

(56) References Cited

U.S. PATENT DOCUMENTS

2007/0092617 A1    4/2007   Burgos et al.

FOREIGN PATENT DOCUMENTS

CN    102781252 A    11/2012
CN    103260424 A    8/2013
(Continued)

OTHER PUBLICATIONS

Bickler, Bob, What is Flash Chromatography and why should I do it?, Biotage, 2019, pp. 1-8. (Year: 2019).*
(Continued)

*Primary Examiner* — Trevor Love
(74) *Attorney, Agent, or Firm* — Dilworth & Barrese, LLP

(57) ABSTRACT

The invention relates to a process for the continuous production of an adsorption product of a nitrooxy-functional organic compound adsorbed on the surface of a particulate adsorbent material, the process comprising the steps of: continuously feeding particulate adsorbent material into an elongated cavity; continuously conveying the material within the cavity in a downstream direction; continuously spraying a liquid adsorbate onto the particulate adsorbent material, wherein the liquid adsorbate comprises the nitrooxy-functional organic compound; continuously agitating the mixture thus obtained to form the adsorption product; and continuously removing the adsorption product from the cavity. The invention further relates to an adsorption product obtained by such process and the use of such adsorption product in ruminant nutrition.

22 Claims, 3 Drawing Sheets

(51) Int. Cl.
*A23K 50/10* (2016.01)
*C07C 203/04* (2006.01)

(56) References Cited

FOREIGN PATENT DOCUMENTS

| | | |
|---|---|---|
| CN | 103561586 A | 2/2014 |
| CN | 105472995 A | 4/2016 |
| WO | 2007/038128 A2 | 4/2007 |
| WO | 2011/070133 A1 | 6/2011 |
| WO | 2012/084629 A1 | 6/2012 |
| WO | 2012/160191 A2 | 11/2012 |
| WO | 2018/091643 A1 | 5/2018 |
| WO | 2018/149755 A1 | 8/2018 |
| WO | 2018/149756 A1 | 8/2018 |

OTHER PUBLICATIONS

Bickler, Bob, So, what exactly is a column volume in flash column chromatography and how is it determined?, Biotage, 2016, pp. 1-10. (Year: 2016).*

Zakarian Group, Technical Notes, Accessed 2022. (Year: 2022).*

* cited by examiner

CONTINUOUS PRODUCTION OF AN ADSORPTION PRODUCT OF A NITROOXY-FUNCTIONAL ORGANIC COMPOUND

BACKGROUND OF THE INVENTION

The invention relates to process for the continuous production of an adsorption product of a nitrooxy-functional organic compound adsorbed on the surface of a particulate adsorbent material. The invention further relates to an adsorption product obtained by such process and its use in ruminant nutrition.

Nitrooxy-functional organic compounds are widely used in animal nutrition to diminish methane production in ruminants. For example, the drug 3-Nitrooxypropanol, abbreviated 3NOP, is an organic compound with the formula HO—CH$_2$—CH$_2$—CH$_2$—O—NO$_2$. It is the mononitrate ester of 1,3-propanediol. The compound is an inhibitor of the enzyme methyl coenzyme M reductase (MCR). MCR catalyzes the final step in methanogenesis. When it is fed to ruminants such as cows, their methane production is diminished and they gain weight. Ruminants are some of the greatest contributors of methane, a significant greenhouse gas. Accordingly, 3NOP is used in agriculture in large quantities.

Ruminant nutrition products have been developed that contain 3NOP in the form of an adsorption product of 3NOP adsorbed on the surface of a particulate adsorbent material. These products were discontinuously produced in batch processes to be able to guarantee homogenous filler loadings and generally high quality. From the viewpoint of production efficiency, however, continuous process settings would be preferable.

SUMMARY OF THE INVENTION

The invention aims to provide a process for the continuous production of a high quality adsorption product of a nitrooxy-functional organic compound adsorbed on the surface of a particulate adsorbent material.

Against this background, the invention relates to a process for the continuous production of an adsorption product of a nitrooxy-functional organic compounds adsorbed on the surface of a particulate adsorbent material, the process comprising the steps of: continuously feeding particulate adsorbent material into an elongated cavity; continuously conveying the material within the cavity in a downstream direction; continuously spraying a liquid adsorbate onto the particulate adsorbent material, wherein the liquid adsorbate comprises a nitrooxy-functional organic compound; continuously agitating the mixture thus obtained to form the adsorption product; and continuously removing the adsorption product from the cavity. Such continuous setting has been found out to yield a high quality adsorption product at increased production efficiency as compared to state of the art methods.

In one embodiment, the particulate adsorbent material is granular silica, charcoal or zeolite material. Granular silica material is preferred in some embodiments. The average grain size of the granular material may be between 10-1000 μm, preferably 50-500 μm and more preferably between 200-400 μm as determined with laser diffraction system dry measurement (Malvern MasterSizer 3000). The inclusive graphic standard deviation of the granular material diameter as expressed in phi units may be smaller 1. The particulate adsorbent material is preferably a porous material. Specifically, it is preferred that the adsorbent material has a specific surface area of at least 100 m$^2$/g and preferably at least 200 m$^2$/g as determined using the BET method according to DIN ISO 9277. In one embodiment, the particulate adsorbent material is a porous material having an oil adsorption capacity of between 100 and 300 ml/100 g, as determined according to DIN ISO 19246.

In one embodiment, the nitrooxy-functional organic compound is a compound of formula (I) below

(I)

wherein n is an integer from 1 to 10; R$^1$ is H, C$_{1-6}$-alkyl, phenyl, —OH, —NH$_2$, —CN, —COOH, —COO$^-$M$^+$, —O(C═O)R$^2$, —NH(C═O)R$^3$, SO$_2$(NH)R$^4$ or —ONO$_2$; R$^2$, R$^3$ and R$^4$ are independently from each other either C$_{1-6}$-alkyl, phenyl or pyridyl, with the proviso that when n is >3 the hydrocarbon chain may be interrupted by —O— or —NH—; and M$^+$ is a metal cation or an ammonium, preferably M$^+$ is sodium (Na$^+$), potassium (K$^+$), lithium (Li$^+$), magnesium (Mg$^{2+}$), calcium (Ca$^{2+}$), barium (Ba$^{2+}$), strontium (Sr$^{2+}$), and ammonium (NH$_4^+$).

As understood above, C$_{1-6}$-alkyl encompasses straight-chain C$_{1-6}$-alkyl, as well as branched C$_{3-6}$-alkyl and cyclic C$_{5-6}$-alkyl. Preferred examples of pyridyl are 2-pyridyl and 3-pyridyl.

In one embodiment, n is an integer from 1 to 7; and/or R$^1$ is —OH, —CN, —ONO$_2$, phenyl, —O(C═O)R$^2$, —NH(C═O)R$^3$, SO$_2$(NH)R$^4$; and/or R$^2$, R$^3$ and R$^4$ are independently from each other either C$_{1-6}$-alkyl, phenyl or pyridyl, with the proviso that when n is >3 the hydrocarbon chain may be interrupted by —O— or —NH—.

In one embodiment, n is an integer from 1 to 5; and/or R$^1$ is —OH, —CN, —ONO$_2$, phenyl, —O(C═O)R$^2$, —NH(C═O)R$^3$, SO$_2$(NH)R$^4$; and/or R$^2$ is phenyl or C$_{1-6}$-alkyl; and/or wherein R$^3$ is pyridyl; and/or R$^4$ is C$_{1-6}$-alkyl, with the proviso that when n is >3 the hydrocarbon chain may be interrupted by —O— or —NH—.

In one embodiment, n is an integer between 3 and 9 and R$^1$ is OH, COOH or —ONO$_2$, with the proviso that when n is >3 the hydrocarbon chain may be interrupted by —O— or —NH—.

Exemplary compounds of formula (I) are 3-nitrooxypropanol (3NOP, CAS-No: 100502-66-7), 9-nitrooxynonanol, 5-nitrooxy pentanoic acid (CAS 74754-56-6), 6-nitrooxy hexanoic acid (CAS 74754-55-5), bis(2-hydroxyethyl)amine dinitrate (CAS 20830-49-3), 1,3-bis-nitrooxypropane, 1,4-bis-nitrooxybutane (CAS 3457-91-8), 1,5-bis-nitrooxypentane (CAS 3457-92-9) and mixtures thereof.

A preferred compound in the context of the present invention is 3-nitrooxypropanol (3NOP; n=3; R$^1$═OH).

The compounds of formula (I) according to the present invention are, in principle, known and either commercially available or can be prepared in analogy to the processes as e.g. disclosed in WO 2012/084629.

In one embodiment, compounds of formula (I) are selected from the list of compounds, and salts thereof comprising: 3-Nitrooxypropanol, racemate-4-Phenylbutane-1,2-diyl dinitrate, 2-(Hydroxymethyl)-2-(nitrooxymethyl)-1,3-propanediol, N-Ethyl-3-nitrooxy-propionic sulfonyl amide, 5-Nitrooxy-pentanenitrile, 5-Nitrooxy-pentane, 3-Nitrooxy-propyl propionate, 1,3-bis-Nitrooxypropane, 1,4-bis-Nitrooxybutane, 1,5-bis-Nitrooxypentane, 3-Nitrooxy-propyl benzoate, 3-Nitrooxy-propyl hexanoate, 3-Nitrooxy-propyl 5-nitrooxy-hexanoate, Benzylnitrate, isosorbid-dinitrate, and N-[2-(Nitrooxy)ethyl]-3-pyridinecarboxamide, 2-Nitro-5-nitrooxymethylfuran, and Bis-(2-nitrooxyethyl) ether as listed in Table 1:

TABLE 1

Exemplary compounds of formula (I)

| Comp. Identifier | Molecular structure | Chemical name |
|---|---|---|
| 1 | HO–––O–NO$_2$ | 3-Nitrooxypropanol |
| 2 | (phenyl–CH$_2$CH$_2$–CH(ONO$_2$)–CH$_2$–ONO$_2$) | rac-4-Phenylbutane-1,2-diyl dinitrate |
| 3 | C(CH$_2$OH)$_3$(CH$_2$ONO$_2$) | 2-(Hydroxymethyl)-2-(nitrooxymethyl)-1,3-propanediol |
| 4 | Et–NH–SO$_2$–(CH$_2$)$_3$–O–NO$_2$ | N-Ethyl-3-nitrooxy-propionic sulfonyl amide |
| 5 | O$_2$N–O–(CH$_2$)$_4$–C≡N | 5-Nitrooxy-pentanenitrile |
| 6 | O$_2$N–O–(CH$_2$)$_4$–CH$_3$ | 5-Nitrooxy-pentane |
| 7 | CH$_3$CH$_2$–C(=O)–O–(CH$_2$)$_3$–O–NO$_2$ | 3-Nitrooxy-propyl propionate |
| 8 | O$_2$N–O–(CH$_2$)$_3$–O–NO$_2$ | 1,3-bis-Nitrooxypropane |
| 9 | O$_2$N–O–(CH$_2$)$_4$–O–NO$_2$ | 1,4-bis-Nitrooxybutane |
| 10 | O$_2$N–O–(CH$_2$)$_5$–O–NO$_2$ | 1,5-bis-Nitrooxypentane |
| 11 | PhC(=O)–O–(CH$_2$)$_3$–O–NO$_2$ | 3-Nitrooxy-propyl benzoate |
| 12 | CH$_3$(CH$_2$)$_4$C(=O)–O–(CH$_2$)$_3$–O–NO$_2$ | 3-Nitrooxy-propyl hexanoate |
| 13 | O$_2$N–O–(CH$_2$)$_4$–C(=O)–O–(CH$_2$)$_3$–O–NO$_2$ | 3-Nitrooxy-propyl 5-nitrooxy-hexanoate |
| 14 | Ph–CH$_2$–O–NO$_2$ | Benzylnitrate |
| 15 | isosorbide dinitrate structure | isosorbid-dinitrate |

TABLE 1-continued

Exemplary compounds of formula (I)

| Comp. Identifier | Molecular structure | Chemical name |
| --- | --- | --- |
| 16 | 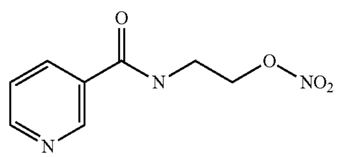 | N-[2-(Nitrooxy)ethyl]-3-pyridinecarboxamide |
| 17 | 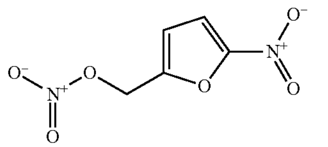 | 2-Nitro-5-nitrooxymethyl-furan |
| 18 | 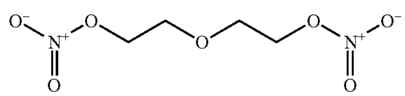 | Bis-(2-nitrooxyethyl) ether |

Preferred compounds of formula (I) based on the strength of their effect in reducing methane are selected from the list of compounds, and salts thereof comprising: 3-Nitrooxypropanol, 5-Nitrooxy-pentanenitrile, 5-Nitrooxy-pentane, 3-Nitrooxy-propyl propionate, 1,3-bis-Nitrooxypropane, 1,4-bis-Nitrooxybutane, 1,5-bis-Nitrooxypentane, 3-Nitrooxy-propyl benzoate, 3-Nitrooxy-propyl hexanoate, 3-Nitrooxy-propyl 5-nitrooxy-hexanoate, isosorbid-dinitrate, and N-[2-(Nitrooxy)ethyl]-3-pyridinecarboxamide, and Bis-(2-nitrooxyethyl) ether as listed in Table 2:

TABLE 2

Preferred compounds of formula (I)

| Comp. Identifier | Molecular structure | Chemical name |
| --- | --- | --- |
| 1 | 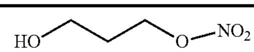 | 3-Nitrooxypropanol |
| 5 | 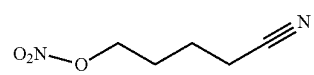 | 5-Nitrooxy-pentanenitrile |
| 6 | 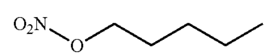 | 5-Nitrooxy-pentane |
| 7 | 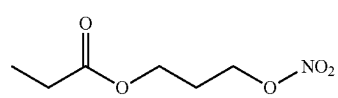 | 3-Nitrooxy-propyl propionate |
| 8 | 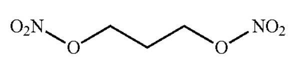 | 1,3-bis-Nitrooxypropane |
| 9 | 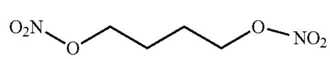 [SMILES: O=[N+]([O-])OCCCCO[N+](=O)[O-]] | 1,4-bis-Nitrooxybutane |
| 10 | 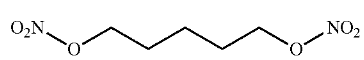 [SMILES: O=[N+]([O-])OCCCCCO[N+](=O)[O-]] | 1,5-bis-Nitrooxypentane |
| 11 | 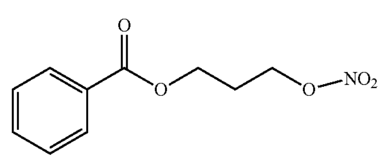 [SMILES: O=C(OCCCO[N+](=O)[O-])c1ccccc1] | 3-Nitrooxy-propyl benzoate |
| 12 | 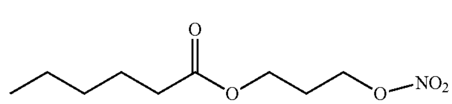 | 3-Nitrooxy-propyl hexanoate |

TABLE 2-continued

Preferred compounds of formula (I)

| Comp. Identifier | Molecular structure | Chemical name |
|---|---|---|
| 13 | $O_2N\diagdown O\diagdown\diagdown\diagdown C(=O)\diagdown O\diagdown\diagdown O\diagdown NO_2$ | 3-Nitrooxy-propyl 5-nitrooxy-hexanoate |
| 15 | (isosorbide dinitrate structure) | Isosorbid-dinitrate |
| 16 | (N-[2-(Nitrooxy)ethyl]-3-pyridinecarboxamide structure) | N-[2-(Nitrooxy)ethyl]-3-pyridinecarboxamide |
| 18 | $O^-\diagdown N^+(=O)\diagdown O\diagdown\diagdown O\diagdown\diagdown O\diagdown N^+(=O)\diagdown O^-$ | Bis-(2-nitrooxyethyl) ether |

In one embodiment, the nitrooxy-functional compound as used in the process of the invention can be a mixture of two or more nitrooxy-functional compounds, preferably a mixture of two or more nitrooxy-functional compounds of formula (I) as defined above.

A suitable combination is a mixture of 3-nitrooxy propanol and 1,3-bis-nitrooxypropane. Preferably the ratio 3-nitrooxy propanol/1,3-bis-nitrooxypropane is comprised between 1/10 and 1000/1, more preferably, between 1/5 and 100/1, most preferably, between 1/1 and 10/1.

In one embodiment, the liquid adsorbate comprises the nitrooxy-functional organic compound in liquid solution, wherein preferably the solvent comprises water, i.e., is pure water, an aqueous solution or a mixture of water with a polar organic solvent, like an alcohol, ketone or the like.

In another embodiment, the solvent can also be an organic solvent, preferably an organic solvent comprising one or more alcoholic groups. Suitable solvents comprise polyols like diols or triols. Diols and especially aliphatic diols like propylene glycol can be particularly preferred.

Mixtures of water and such organic solvents can also be suitable in this context.

In one embodiment, the concentration of the nitrooxy-functional organic compound in the solution is between 10-40 wt. %. In some embodiments, concentrations of 15-30 wt % are preferred.

In another embodiment, the liquid adsorbate comprises the nitrooxy-functional organic compound in its pure form, i.e., as an essentially solvent-free liquid compound. For example, the substance 3-Nitrooxypropanol (3NOP, a drug given to ruminants to reduce methane emission) is a liquid at room temperature and could hence also be atomized in its pure form. It may be that these pure compounds comprise some residual solvent, e.g., less than 10 wt % or less than 5 wt % or less than two wt % of solvents, e.g., solvents as described above.

In one embodiment, the average residence time of the particulate material in the cavity is adjusted to be between 2 and 15 minutes and preferably between 5 and 10 minutes. At a given cavity layout, the residence time can be adjusted by varying the particulate adsorbent material feed rate and, in the case of active conveying, the conveying speed. Depending on cavity volume, exemplary particulate adsorbent material feed rates can exceed 100, 500, 1.000 or even 5.000 kg/h.

In one embodiment, the ratio of the introduction rate of liquid adsorbate to the introduction rate of particulate adsorbent material is between 60 and 140 ml, preferably between 80 and 120 ml of liquid adsorbate per 100 g particulate adsorbent material. These ratios may be employed in the process of the invention to obtain a product of sufficiently high and homogenous load. Generally, the ratio should be balanced and consider the adsorption capacity of the material pair.

In one embodiment, the sprayed liquid adsorbent has a temperature of between 10 and 40° C. and/or wherein the liquid adsorbent is sprayed through one or more nozzles and/or wherein the spray pressure of the liquid adsorbent is between 3 and 9 bar. The temperature can be room temperature or the liquid can be preheated or precooled. The temperature has an influence on viscosity and hence spraying behavior. In some applications, viscosities between 10 and 500 mPa·s and preferably between 50 and 200 mPa·s may be considered ideal.

In one embodiment, the cavity has a tubular shape and/or wherein the L/D (length/diameter) ratio of the cavity is between 2 and 10, preferably between 3 and 7. The total volume of the cavity can, in one example, be between 0.1 and 2 m$^3$, but smaller or larger volumes are also possible. Such layouts may be used to obtain a product of sufficiently high and homogenous load. A too small ratio or too large volume may deteriorate product quality. A too large ratio or too small volume may decrease process efficiency.

In one embodiment, the cavity comprises an initial transport zone where the particulate adsorbent material is actively conveyed in a downstream direction, preferably by a screw conveyor, and wherein the cavity comprises a mixing zone where the liquid adsorbate is sprayed onto the particulate adsorbent material and the mixture thus obtained is agitated by mixing instruments to form the adsorption product, preferably by mixing instruments such as mixing paddles that are mounted on a shaft that extends through the cavity in a longitudinal direction.

The process may be carried out in an apparatus that includes a mixing drum comprising the elongated and preferably tubular cavity with an upstream adsorbent inlet, a downstream product outlet and one or more injection nozzles for spraying the liquid adsorbate. A rotating member may extend through the cavity in its longitudinal direction. It may comprise at least one helical conveying blade to form a screw conveyor in one longitudinal zone of the cavity and mixing instruments in another longitudinal zone of the cavity.

The mixing instruments such as mixing paddles are preferably distributed over the length of the mixing zone. The distribution can be regular or irregular. In one embodiment, the operative surfaces of the paddles are slanted backwards. In other words, the operative surfaces of the paddles are not parallel to the longitudinal direction cavity but are slanted to effect reverse movement of the particulate material. Such reverse mixing can beneficially influence adsorption quality and homogeneity. Other suitable mixing instruments that may be used alternatively to or in conjunction with mixing paddles comprise screw fragments.

In one embodiment, the cavity comprises an intermediate transport zone within the mixing zone, where premixed material is actively conveyed in a downstream direction from a primary to a secondary mixing zone, preferably by another screw conveyor. In this embodiment, the liquid adsorbate is sprayed onto the particulate adsorbent material in the primary mixing zone prior intermediate transport.

In an alternative embodiment, the secondary mixing zone can be replaced by a resting zone without mixing paddles.

In one embodiment, the cavity comprises a terminal transport zone where product material is actively conveyed in a downstream direction from the mixing zone to the outlet, preferably by another screw conveyor.

Indications as made above regarding the cavity altogether, such as average residence times, L/D ratio, cavity volume, or the like may in one embodiment more specifically apply to the mixing zone or mixing zones of the cavity.

In one embodiment, the screw conveyor and/or shaft-mounted mixing elements are operated at a rotational speed such that the peripheral speed of the screw conveyor and/or shaft-mounted mixing elements is 1 m/s or less. These low peripheral speeds can be preferred to avoid excessive frictional heat that may negatively affect potentially heat-sensitive nitrooxy-functional organic compound and unwanted dust formation due to grinding of the particulate materials. The risk of smoldering, fires and dust explosions can thereby be minimized. The peripheral speed as defined above relates to the point of highest radial extension. Depending on the radius of the cavity, such can correspond to rotational speeds of, e.g., less than 50 rpm.

In one embodiment, the cavity is inclined in downstream direction, wherein the incline angle is preferably between 15 and 45° and/or wherein the cavity is partially filled with material, wherein preferably the mixing zone comprises a subsection that is fully filled with material and a subsection that is partially filled with material. It can be provided that the incline angle and the length and diameter of the mixing zone are such that there are longitudinal positions within the mixing zone whose entire cross-section remains below the level of product removal, and preferably such that longitudinal positions whose entire cross-section remains below the level of product removal account for at least 30% of all longitudinal positions within the mixing zone.

In one embodiment, the liquid adsorbate is sprayed onto the particulate adsorbent material at a longitudinal position of the cavity where it is fully filled with particulate adsorbent material and/or wherein the cavity volume unoccupied by the particulate material is filled with ambient air. In other words, no inert gas blanket is introduced to the cavity. Dust formation and flammable vapor may largely be avoided by the continuous process where the liquid adsorbate is directly sprayed onto the adsorbent material and the mixture is conveyed through an elongated cavity. Inert gas may hence not be needed to avoid any explosion risk, even when using flammable materials.

The invention further relates to an adsorption product of a nitrooxy-functional organic compound adsorbed on the surface of a particulate adsorbent obtained by the process of the invention and the use of such adsorption product in ruminant nutrition.

BRIEF DESCRIPTION OF THE DRAWINGS

Further details and advantages of the invention will be explained in the following with reference to the figures and working examples. The figures show.

DESCRIPTION OF THE PREFERRED EMBODIMENTS

Figure 1:
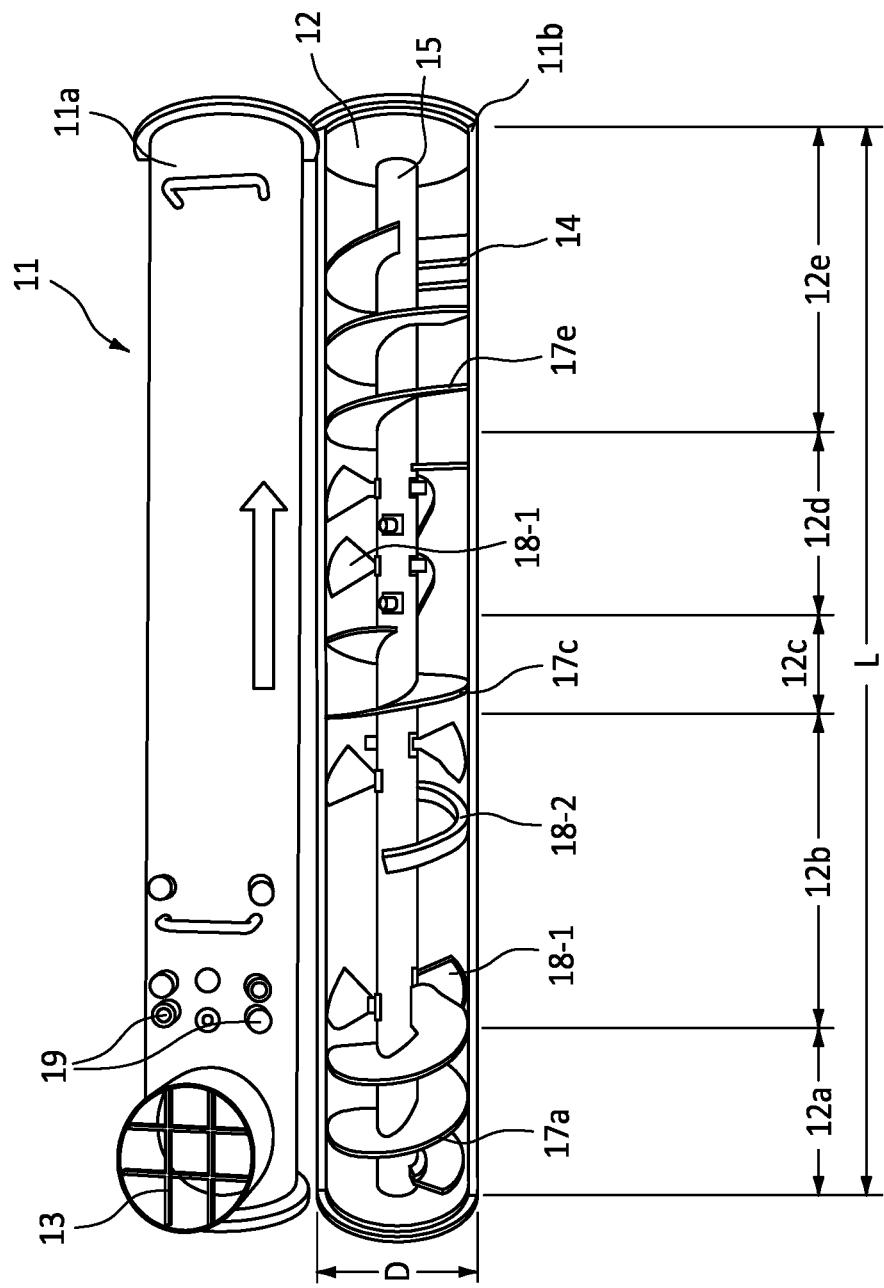
FIG. 1: a longitudinal section of a mixing drum that may be used to carry out a process of the invention.

In FIG. 1 a mixing drum that may be used to carry out a process of the invention is schematically illustrated. The mixing drum 11 is generally tubular in shape and has an elongated tubular cavity 12 of essentially circular cross-section for receiving the particulate granular adsorbent material. On the upstream end of the cavity 12, an adsorbent inlet opening 13 is provided on the upper side of the cavity wall. On the downstream end of the cavity 12, a product outlet opening 14 is provided on the lower side of the cavity wall. The mixing drum 11 is made of stainless steel and consists of two halves, a base 11a and a lid 11b. The inlet opening 13 is arranged at the lid 11b. The outlet opening 14 is arranged at the base 11a. The overall length L of the cavity 12 is 140 cm and the diameter D is 20 cm, accounting for an L/D ratio of 7.0 and a total chamber volume of 0.044 m$^3$.

Figure 2:
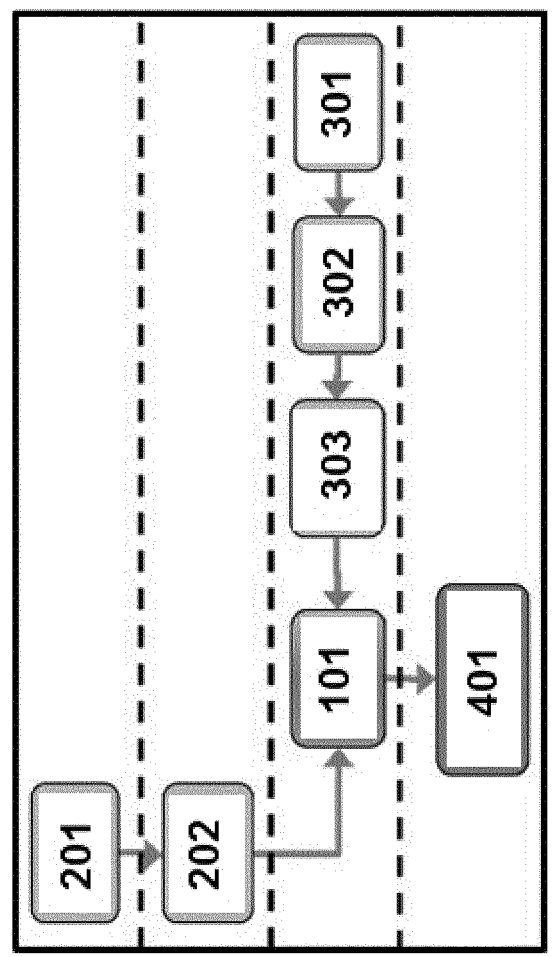
FIG. 2: a flow diagram illustrating the process of the invention.

The inlet opening 13 may be connected to a feeding apparatus for continuously introducing a controlled amount of granular adsorbent material to the cavity 12, such as a suitable gravimetric loss-on-weight type powder feeder. Such is apparent from the flow diagram of FIG. 2, where the mixing step 101 that is carried out in the apparatus 10 is preceded, on the one hand, by a step 201 of charging a feeder from a granular adsorbent material reservoir and a step 202 of feeding the granular adsorbent material to the inlet 13.

A rotating shaft 15 extends through the cavity in longitudinal direction. The shaft 15 is arranged in the center of the circle defined by the cross-section of the cavity 12 and is operably connected to an electric motor for driving the shaft 15 at a desired rotation speed. The regular rotation direction of the shaft 15 is counterclockwise, when looking in the direction of the product flow that is symbolized in FIG. 1 by the arrow.

The rotating shaft 15 comprises two types of rotating annexes that are distributed over the length of the cavity 12, namely helical conveying blades 17a, 17c and 17e as well as mixing instruments 18-1 and 18-2b. The helical conveying blade 17a is arranged around the shaft 15 in the initial transport section 12a of the cavity 12 that is adjacent to the inlet opening 13. The mixing instruments 18-1 and 18-2 are distributed within primary and secondary mixing zones 12b and 12d that follow the initial transport section 12a. The primary and secondary mixing zones 12b and 12d are separated by an intermediate transport zone 12c, where the helical conveying blade 17c is arranged around the shaft 15. The intermediate transport zone 12c is rather short and the number of full rotations of the helical conveying blade 17c around the shaft 15 is less than two. The mixing zones 12b and 12d are followed by a terminal transport zone 12e, where the helical conveying blade 17e is arranged around the shaft 15.

The mixing instruments comprise a number of pairs of mixing paddles 18-1, wherein the individual paddles 18-1 of the pairs are slightly offset in longitudinal direction. Specifically, in the primary mixing zone 12b, two helical mixing blade fragments 18-2 are arranged between the pairs. In contrast to the helical conveying blades 17a, 17c or 17e, the blade fragments 18-2 do not comprise a closed surface but rather an open construction such as to limit the feeding forward action. The secondary mixing zone 12d only comprises mixing paddles 18-1.

In an alternative embodiment, the secondary mixing zone 12d can be replaced by a resting zone without mixing paddles 18-1 or blade fragments 18-2.

The apparatus 10 further comprises injection nozzles 19 for injecting a liquid adsorbate to the cavity 12, and more specifically to an early position within the primary mixing zone 12b. Specifically, the nozzles 19 are arranged at a longitudinal position corresponding to the upstream pair of mixing paddles 18. The injection nozzles 19 are connected to a suitable liquid supply that includes a tank, a heating, a liquid pump and a volume flow meter whose signal is used to regulate pump operation. Such, again, is apparent from the flow diagram of FIG. 2, where the mixing step 101 is also preceded by a step 301 of suctioning liquid adsorbate from a liquid adsorbate tank and, optionally, preheating the liquid adsorbate to a desired temperature, a step 302 of pumping the liquid adsorbate to the nozzles 19 and a step 303 of measuring the volume flow towards the nozzles 19.

The rotating shaft 15 and the rotating annexes 17a, 17c, 17e, 18-1 and 18-2 are all made of stainless steel. The injection nozzles 19 are arranged at the lid 11b. The rotating shaft 15 and motor are arranged at the base 11a.

The outlet opening 14 can be connected to a suitable packaging apparatus for weighting and packaging the product. Also this is apparent from the flow diagram of FIG. 2, where the mixing step 101 is followed by a packaging step 401.

A lifting means including, for example, suitable swivel joints and a hydraulic cylinder may be used to lift the end section of the tubular mixing drum 11 to adjust a certain incline of the tubular cavity 12. In consideration of such incline, the primary and secondary mixing zones 12b and 12d can further be subdivided in fully filled sections and partially filled sections. Specifically, owing to the essentially fluid behavior of suitable granular adsorbent materials, the materials will form an essentially planar surface within the cavity 12. The surface level corresponds essentially to the level of the lowest points of action of the helical conveying blades 17c and 17e, respectively, as any fluidly behaving material that reaches these levels will be transported further by the blade 17c or 17e. The longitudinal position of the boundary between the fully filled and partially filled sections hence depends on the ratio of length to diameter of the mixing zones 12b and 12d as well as on the incline angle of the cavity 12. In this regard, the incline angle is preferably set such that the injection nozzles 19 are arranged at an early position within the primary mixing zone 12b that is fully filled in operation.

In an experimental setup, the mixing drum as shown in FIG. 1 was loaded with a particulate silica material with a nominal median particle size of between 45-50 µm and a solution of 23% of 3-Nitrooxypropanol (3NOP, a drug given to ruminants to reduce methane emission) dissolved in 77% propylene glycol solvent as liquid adsorbent material. The weight ratio of the granular silica material and the liquid adsorbent material was 50/50. The inclination of the cavity 12 was set to 33°. The rotation speed of the shaft was set to 45 rpm, which led to a peripheral speed of the rotating annexes 17a, 17c, 17e, 18-1 and 18-2 of around 0.5 m/s. Nozzle pressure was 6 bar. Silica temperature was 27° C.

Using these settings, the filled chamber volume was determined at 0.017 $m^3$, corresponding to approx. 38% of the total chamber volume. The feed rates (granular material) necessary to attain certain average residence times (standard deviation is about 40%) as determined in this experiment are outlined in Table 1 below.

TABLE 1

| Residence time | Feed rate |
| --- | --- |
| 2 min 30 sec | 249 kg/h |
| 5 min | 124 kg/h |
| 7 min | 89 kg/h |
| 10 min | 62 kg/h |

Figure 3:
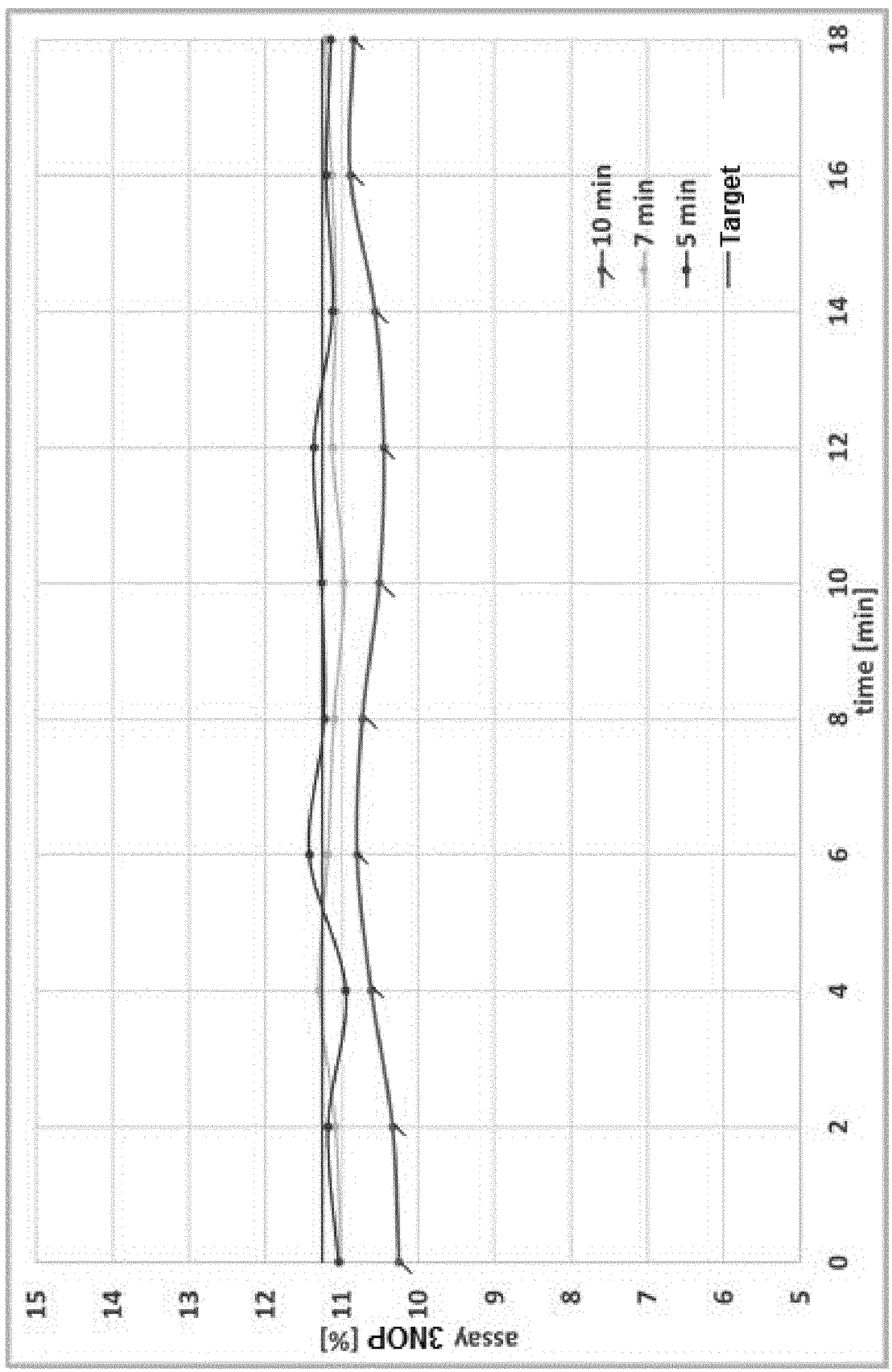
FIG. 3: an assay showing the surface loading of 3NOP over process time at different residence times.

In FIG. 3 an assay is shown that illustrates the surface loading of 3NOP over process time at different residence times. While it would be expected that lowering the residence times have a negative impact on the adsorption homogeneity, the assay shows indeed very good adsorption homogeneity even at an average residence time of only 2 min 30 sec. Accordingly, scaling calculations would suggest that an output of several tons of product per hour would be attainable with bigger mixers having a chamber volume of, for example, between 0.1 and 2 $m^3$. Such scaling calculations for commercially available mixers are shown in Table 2 below.

TABLE 2

| | Pilot Mixer | Ruberg DLM 350-1500 | | | Ruberg DLM 800-3000 | | |
| --- | --- | --- | --- | --- | --- | --- | --- |
| L[m] | 1.4 | 1.5 | | | 3.0 | | |
| D[m] | 0.2 | 0.35 | | | 0.8 | | |
| L/D | 7.0 | 4.3 | | | 3.8 | | |
| chamber [$m^3$] volume | 0.0044 | 0.144 | | | 1.507 | | |
| filled [%] chamber | 38 | 38 | 50 | 75 | 38% | 50% | 75% |

TABLE 2-continued

| | Pilot Mixer | Ruberg DLM 350-1500 | | | Ruberg DLM 800-3000 | | |
|---|---|---|---|---|---|---|---|
| [m³] volume | 0.017 | 0.055 | 0.072 | 0.108 | 0.573 | 0.754 | 1.130 |
| feed rate at residence time [kg/h] | | | | | | | |
| 2.5 min | 249 | 816 | 1.073 | 1.610 | 8.522 | 11.214 | 16.820 |
| 5 min | 124 | 408 | 537 | 805 | 4.261 | 5.607 | 8.410 |
| 7 min | 89 | 291 | 383 | 575 | 3.044 | 4.005 | 6.007 |
| 10 min | 62 | 204 | 268 | 402 | 2.131 | 2.803 | 4.205 |

Similar assays have demonstrated no difference in loading and homogeneity between adsorbate temperatures of 15° C., 25° C. and 35° C.

The invention claimed is:

1. A process for the continuous production of an adsorption product of a nitrooxy-functional organic compound adsorbed on the surface of a particulate adsorbent material, comprising the steps of:
providing a mixing drum comprising an elongated cavity;
continuously feeding particulate adsorbent material into the elongated cavity;
continuously conveying the material within the elongated cavity in a downstream direction;
continuously spraying a liquid adsorbate onto the particulate adsorbent material, wherein the liquid adsorbate comprises the nitrooxy-functional organic compound;
continuously agitating the mixture thus obtained to form the adsorption product; and
continuously removing the adsorption product from the cavity,
wherein the elongated cavity comprises an initial transport zone where the particulate adsorbent material is conveyed in the downstream direction, and a mixing zone where the liquid adsorbate is sprayed onto the particulate adsorbent material and the mixture thus obtained is continuously agitated by mixing instruments to form the adsorption product,
the liquid adsorbate is continuously sprayed onto the particulate adsorbent material as the adsorbent material is conveyed along the elongated cavity in the downstream direction, and
the particulate adsorbent material is conveyed in the downstream direction by a screw conveyor in a continuous manner, and the mixing instruments are mixing paddles mounted on a shaft, said shaft extending through the elongated cavity in a longitudinal direction.

2. The process of claim 1, wherein the particulate adsorbent material is granular silica, charcoal or zeolite material having average grain size between 10-1000 μm.

3. The process of claim 1, wherein the particulate adsorbent material is a porous material having a specific surface area of at least 100 m²/g and/or an oil adsorption capacity of between 100 and 300 ml/100 g.

4. The process of claim 1, wherein the nitrooxy-functional organic compound is a compound of formula (I) below

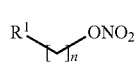

(I)

wherein n is an integer from 1 to 10; R1 is H, C1-6-alkyl, phenyl, —OH, —NH2, —CN, —COOH, —COO-M+, —O(C═O)R2, —NH(C═O)R3, SO2(NH)R4 or —ONO2; R2, R3 and R4 are independently from each other either C1-6-alkyl, phenyl or pyridyl, with the proviso that when n is >3 the hydrocarbon chain may be interrupted by —O— or —NH—; and M+ is a metal cation or an ammonium.

5. The process of claim 4, wherein the nitrooxy-functional organic compound is one selected from 3-nitrooxypropanol, 9-nitrooxynonanol, 5-nitrooxy pentanoic acid, 6-nitrooxy hexanoic acid, bis(2-hydroxyethyl)amine dinitrate, 1,3-bis-nitrooxypropane, 1,4-bis-nitrooxybutane, 1,5-bis-nitrooxypentane and mixtures thereof.

6. The process of claim 4, wherein the nitrooxy-functional organic compound is a mixture of two or more nitrooxy-functional compounds of formula (I).

7. The process of claim 1, wherein the liquid adsorbate comprises the nitrooxy-functional organic compound in liquid solution.

8. The process of claim 1, wherein average residence time of the particulate material in the cavity is between 2 and 15 minutes and/or ratio of introduction rate of liquid adsorbate to introduction rate of particulate adsorbent material is between 60 and 140 ml of liquid adsorbate per 100 g particulate adsorbent material.

9. The process of claim 1, wherein the sprayed liquid adsorbent has a temperature of between 10 and 40° C., and/or the liquid adsorbent is sprayed through one or more nozzles, and/or spray pressure of the liquid adsorbent is between 3 and 9 bar, and/or the cavity has a tubular shape, and/or L/D (length/diameter) ratio of the cavity is between 2 and 10.

10. The process of claim 1, wherein the screw conveyor and/or shaft-mounted mixing elements are operated at a rotational speed such that the peripheral speed of the screw conveyor and/or shaft-mounted mixing elements is 1 m/s or less.

11. The process of claim 1, wherein the cavity is inclined in downstream direction, and/or the cavity is partially filled with material.

12. The process of claim 2, wherein the particulate adsorbent material is granular silica material with average grain size between 50-500 μm.

13. The process of claim 12, wherein the average grain size is between 200-400 μm.

14. The process of claim 3, wherein the particulate adsorbent material has a specific surface area of at least 200 m²/g.

15. The process of claim 4, wherein M+ is sodium (Na+), potassium (K+), lithium (Li+), magnesium (Mg2+), calcium (Ca2+), barium (Ba2+), strontium (Sr2+), or ammonium (NH4+).

16. The process of claim 5, wherein the nitrooxy-functional organic compound is 3-nitrooxypropanol (3NOP; n=3; R1=OH).

17. The process of claim 6, wherein the nitrooxy-functional organic compound is a mixture of 3-nitrooxy propanol and 1,3-bis-nitrooxypropane.

18. The process of claim 7, wherein solvent in the liquid solution comprises water, and/or concentration of the nitrooxy-functional organic compound in the solution is between 10-40 wt. %.

19. The process of claim 8, wherein the average residence time of the particulate material in the cavity is between 5 and 10 minutes and/or the ratio of the introduction rate of liquid adsorbate to the introduction rate of particulate adsorbent material is between 80 and 120 ml of liquid adsorbate per 100 g particulate adsorbent material.

20. The process of claim 9, wherein the L/D (length/diameter) ratio of the cavity is between 3 and 7.

21. The process of claim 11, wherein the incline angle is between 15 and 45°, and/or the mixing zone comprises a subsection that is fully filled with material and a subsection that is partially filled with material.

22. The process of claim 21, wherein the liquid adsorbate is only sprayed onto the particulate adsorbent material at a longitudinal position of the cavity where it is fully filled with particulate adsorbent material, and cavity volume unoccupied by the particulate material is filled with only ambient air, preventing an inert gas blanket from being introduced into the cavity.

\* \* \* \* \*